United States Patent [19]

Langer et al.

[11] Patent Number: 4,613,661

[45] Date of Patent: Sep. 23, 1986

[54] EPOXY PHOSPHATE COMPOSITIONS

[75] Inventors: Horst G. Langer, Wayland; Thomas P. Brady, Holliston; Marsha A. Paul, Natick; George A. Doorakian, Bedford, all of Mass.

[73] Assignee: The Dow Chemical Company, Midland, Mich.

[21] Appl. No.: 738,325

[22] Filed: May 28, 1985

[51] Int. Cl.$^4$ ............................................. C08G 59/30
[52] U.S. Cl. ................................. 528/108; 525/523; 528/99; 528/398; 549/219
[58] Field of Search ................. 549/219; 528/108, 99, 528/398; 525/523

[56] References Cited

U.S. PATENT DOCUMENTS

| | | |
|---|---|---|
| 2,541,027 | 2/1951 | Bradley . |
| 2,866,680 | 12/1958 | Long . |
| 2,887,404 | 5/1959 | Evans ............................. 528/108 X |
| 3,245,940 | 4/1966 | Ronay et al. .................... 528/108 X |
| 3,578,632 | 5/1971 | Kuhlkamp et al. ............. 528/108 X |
| 3,639,545 | 2/1972 | Wilcox . |
| 3,652,743 | 3/1972 | Harris et al. . |
| 4,164,487 | 8/1979 | Martin . |
| 4,256,844 | 3/1981 | Martin et al. . |
| 4,287,131 | 9/1981 | Langer et al. . |
| 4,289,812 | 9/1981 | Martin . |
| 4,301,025 | 11/1981 | Brady et al. . |
| 4,316,922 | 2/1982 | Perine et al. ........................... 428/35 |
| 4,396,555 | 8/1983 | Brady et al. . |
| 4,397,970 | 8/1983 | Campbell et al. . |
| 4,425,451 | 1/1984 | Sekmakas et al. . |
| 4,497,946 | 2/1985 | Sekmakas et al. .............. 528/108 X |

*Primary Examiner*—Earl Nielsen
*Attorney, Agent, or Firm*—P. D. Hayhurst

[57] ABSTRACT

A process for preparing a phosphate ester which contains at least one terminal epoxide moiety, the process comprising contacting under reaction conditions, optionally in the presence of water, at least one phosphoric acid ester with an amount of an epoxide having an epoxy equivalent greater than one. The product compositions can be cured by standard epoxide curing agents to provide protective coatings having intumescent properties.

21 Claims, No Drawings

EPOXY PHOSPHATE COMPOSITIONS

BACKGROUND OF THE INVENTION

The present invention relates to phosphate ester compounds containing terminal vicinal epoxide functionality, and a process for the preparation of these compounds. More particularly, the present invention relates to hydrolytically stable compositions of matter comprising the reaction product of an epoxide, such as a diglycidyl ether of a dihydroxy compound, and a phosphoric acid ester. The compositions are readily cured by known epoxy curing agents such as amines and anhydrides to form coatings and cast articles. The cured compositions of the present invention are highly useful due to their ability to form char upon application of heat, thereby finding use in intumescent paints and in ablative coatings. Accordingly, a further species of the present invention is an intumescent coating comprising the above phosphate ester compounds containing terminal vicinal epoxide functionality. Said intumescent coatings exhibit improved adhesion to metal and glass substrates.

In U.S. Pat. No. 2,541,027, cured coatings are prepared by the reaction of epoxy ethers such as the diglycidyl ether of bisphenol A with orthophosphoric acid or a monoalkyl orthophosphate. The curing reaction was initiated by mixing together the epoxy resin and the phosphorus-containing curing agent and heating the resulting mixture at an elevated temperature to totally eliminate all epoxide functionality.

In U.S. Pat. No. 4,256,844; 4,289,812; 4,164,487; and 4,316,922, additional adducts of phosphoric acid and epoxides that form water-dispersible neutralized adducts are described. In each reference, the epoxide functionality is completely ring-opened thereby forming secondary hydroxyl-containing compositions. Curing such ring-opened compositions was effected by reaction with hydroxyl curing agents such as isocyanates.

In U.S. Pat. No. 4,425,451, monoesters of orthophosphoric acid and epoxy ethers such as the diglycidyl ether of bisphenol A were prepared by reaction of the ether with 85 percent orthophosphoric acid (in water) in the presence of 2-butoxyethanol solvent. Residual phosphoric acid functionality was neutralized by salification with an amine.

The presence of reactive phosphoric acid moieties in previously known processes has resulted disadvantageously in the formation of various cyclic phosphorus-containing epoxy functionalized esters of phosphoric acid. See U.S. Pat. No. 3,639,545 and 3,652,743. In addition, it has been found that gelling of the resin results by means of reaction between phosphoric acid functionality and epoxide thereby resulting in a loss of epoxide values over time.

In view of the deficiencies of the prior art processes, it would be desirable to provide a process for effectively preparing epoxy derivatives of monoesters of phosphoric acid in high yields. Additionally, it would be desirable to provide a process for preparing epoxy derivatives of phosphoric acid esters that are relatively unaffected by epoxide degradation during storage.

SUMMARY OF THE INVENTION

According to the present invention there is provided a composition comprising a novel, hydrolytically stable phosphate ester containing at least one terminal vicinal epoxide moiety, and a process for the preparation thereof. Preferred phosphate esters of the present invention are represented generally by the formula:

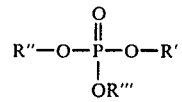

wherein R' is a glycidyl ether of the general formula:

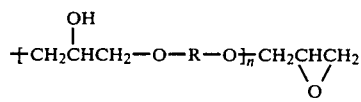

wherein
R is a difunctional remnant of a dihydroxy compound formed by removal of the hydroxyl groups thereof;
R" is a group as defined by R''' or R';
R''' is H or an organic group of up to about 20 carbons; and
n is a positive number less than about 20 and is equal to the number of repeating units in the compound.

In another sense, the invention is a process comprising contacting under reaction conditions, optionally in the presence of water, at least one phosphoric acid ester with an amount of an epoxide having an epoxy equivalent greater than one, said amount being sufficient to substantially neutralize the phosphoric acid functionality of the phosphoric acid ester, the contacting being such that there is formed a composition comprising a phosphate ester containing terminal epoxide functionality corresponding to a compositon described hereinbefore.

Surprisingly, compositions of the present invention can be cured via the epoxide moieties to form a resin having intumescent properties and having good adhesive properties.

DETAILED DESCRIPTION OF THE INVENTION

The compositions prepared according to the process of the present invention are vicinal epoxy terminated thermoplastic advanced resins that are cured to solid objects by conventional amine, carboxylic acid or anhydride functional epoxy curing agents. These storage stable thermoplastic epoxy resins desirably are further characterized by a phosphorus content of from about 0.5 to about 2.6 weight percent and an epoxide content of from about 5 to about 20 percent by weight. Preferred is a process that prepares a resin having a phosphorus content of from about 0.75 to about 1.5 weight percent and an epoxide content, after storage at about 30° C. for 30 days in the presence of air, of from about 4.5 to about 18 percent by weight.

The process of the present invention basically requires contacting a phosphoric acid monoester with an amount of an epoxy compound having an epoxy functionality greater than one sufficient to substantially neutralize the phosphoric acid functionality. An excess of the epoxy compound, which preferably is an epoxy ether, desirably is employed. In a preferred process, the phosphoric acid monoester is prepared by hydrolyzing an organic-soluble pyrophosphate diester. Water is employed in a preferred process of the invention. However, in all processes the amount of water present is such that not all epoxy moieties of the final product resin are hydrolyzed, i.e., the product of the invention contains terminal epoxy moieties.

The term phosphoric acid ester as used herein includes monophosphate polyesters, such as diesters, triesters, etc.; polyphosphate polyesters, such as diphosphate diesters; and monophosphate monoesters. Of these, the monoesters desirably are the esters contacted with an excess of epoxy compound.

A preferred process comprises the steps of:

(1) forming an organic-soluble pyrophosphate diester corresponding to the formula:

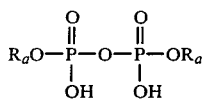

wherein $R_a$ is an organic group of up to about 20 carbon atoms, in an organic solvent;

(2) contacting the organic-soluble pyrophosphate diester with from about 1 to about 16 moles of water per mole of pyrophosphate diester to form the corresponding phosphoric acid monoesters; and (3) contacting the phosphoric acid monoesters of step (2) with an amount of an epoxy ether having an epoxy functionality greater than one sufficient to substantially neutralize the phosphoric acid functionality.

According to a preferred process of the present invention, it is believed that previously described steps (1) and (2) result in the formation of a stable organic solvent-soluble orthophosphate monoester (phosphoric acid monoester) corresponding to the formula:

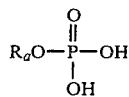

wherein $R_a$ is as previously defined. The preparation of such organic solvent-soluble, stable monoesters has heretofore been accomplished only with great difficulty and in unacceptable yields. It has now been discovered that these monoesters are readily prepared in highly stable form by hydrolyzing the corresponding diester of diphosphoric acid (alternatively referred to as the diester of pyrophosphoric acid).

The diester starting reactants of the preferred process can be conveniently prepared by the reaction of phosphorus pentoxide with about 2 moles per mole of phosphorus pentoxide of an alkanol, phenol, an alkyl or phenyl monoether of a (poly)alkylene glycol, an inertly-substituted derivative of such compounds, or mixtures thereof (referred to hereinafter as hydroxyl-containing reactant). The preparation can be conveniently performed under inert atmosphere by contacting the hydroxyl-containing reactant with a slurry of phosphorus pentoxide in an inert solvent. Preferred inert solvents are chlorinated hydrocarbons, e.g., chloroform, ethylene chloride, methylene chloride, etc. A preferred solvent is methylene chloride. Such diesters of diphosphoric acid and the method of their preparation have been previously described in U.S. Pat. No. 4,396,555. The presence of the organic ether moiety ($R_a$) in the prepared compounds renders the invented compositions more soluble in the above-described organic solvents than previously known epoxy derivatives of phosphorus compounds. Preferably $R_a$ is alkyl or alkoxyalkyl. Examples of typical $R_a$ moieties include phenyl, t-butyl, neopentyl, isopropyl, decyl, butoxyethyl, ethoxyethyl, dimethylaminoethyl, methoxyethyl, and the like. Most preferably, $R_a$ is a glycol ether.

The hydrolysis, step (2) of the previously described preferred process, preferably is performed by contacting the above diester of diphosphoric acid with water at or below ambient temperature. Preferred addition temperatures, i.e., initial contacting temperatures, are from about 0° C. to about 25° C. The hydrolysis can be effected by merely contacting the pyrophosphate diester and water, optionally with heating. Typically, heating is not required due to the exothermic nature of the hydrolysis reaction of step (2). Preferably the organic solvent used in the preparation of the pyrophosphate diester is recovered by distillation or other suitable means and the hydrolysis (step (2)) is conducted in the substantial absence of an organic solvent. The water for the hydrolysis reaction is typically added in a molar amount which is from about 1 to about 16 times the molar amount of diester of diphosphoric acid to be hydrolyzed. Preferably from about 2 to about 12 moles of water are employed for each mole of diester. Most preferably from about 4 moles of water to about 10 moles of water for each mole of diester are employed.

The exothermic hydrolysis reaction is allowed to proceed to substantial completion, which is identified by a reduction in the amount of heat evolved. Typically, the reaction is allowed to proceed until the reaction mass returns to ambient temperature. Usually, completion of hydrolysis requires from about 3 to about 24 hours depending on the reaction conditions employed. In the preferred process, the hydrolyzed reaction product comprising substantial amounts of the desired monoester of orthophosphoric acid is thereafter contacted with the epoxy ether having an epoxy equivalency greater than one.

It is preferred to first hydrolyze the pyrophosphoric acid diester by reaction with excess water prior to reaction with the epoxy ether according to the previously described preferred process in order to reduce the formation of cyclic epoxy phosphate species thought to correspond to the following formula:

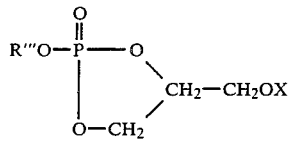

wherein R''' is as previously defined and X is the remnant of the epoxy ether,

after ring-opening of one epoxide functionality has occurred. When excess water is employed to effect hydration as previously explained, the occurrence of the above undesired species is largely eliminated. On the other hand, the presence of alcohol or glycol ether solvents along with the epoxy ether reactant has been found to reduce the theoretical epoxide content of the resulting resin due to competitive reactions between the epoxide and alcohol functionality. Accordingly, it is preferred that the reaction of the epoxy ether with the phosphate ester be conducted in the substantial absence of an organic solvent. However, in certain instances, such as in the preparation of very viscous products, it can be desirable to employ a diluent, such as toluene, hexane or a reactive diluent, such as an aliphatic monoepoxide.

Suitable epoxy ethers include those previously known and taught, for example, in US 2,541,027. Preferred epoxy ether compositions correspond to the formula:

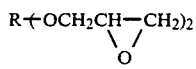

wherein R is as previously defined. Preferably R is an alkylene, arylene, aralkylene or bisaralkylene radical of up to about 30 carbons optionally inertly-substituted. The most preferred epoxy ethers are the diglycidyl ethers of bisphenol compounds, especially the diglycidyl ether of bisphenol A and partially advanced homopolymers thereof.

It has been found that an excess of epoxy ether compound is desirable to prepare a composition that is stable to ring-opening and does not produce gelled reaction products. Suitably, from about 4 equivalents to about 20 equivalents of epoxy ether per equivalent of ester reactant are employed. Preferably, from about 6 equivalents to about 12 equivalents of epoxy ether for each equivalent of ester are employed. The reaction is performed by adding the orthophosphate ester compound to an excess of the epoxy ether accompanied by vigorous agitation to prevent localized stoichiometric imbalance.

The reaction between the epoxy ether and monophosphate ester is preferably conducted at elevated temperatures. Most preferred temperatures are from about 25° C. to about 80° C. By using elevated temperatures and an excess of epoxy ether reactant, phosphorus acid moieties capable of functioning as curing agents for cross-linking (cf. U.S. Pat. No. 2,541,027) are substantially eliminated. Resins according to the present invention are extremely stable in the absence of additional epoxy curing agents.

In the present invention, the amount of epoxy ether having an epoxy functionality greater than one sufficient to substantially neutralize remnant hydroxyl functionality of the hydrolyzed pyrophosphoric acid diesters is defined as the amount necessary to result in a free-flowing, organic-soluble product that is stable under normal conditions of storage. Accordingly, as a test of such storage stability, the material should not form appreciable amounts of epoxide ring-opened degradation products upon exposure for 30 days to temperatures of about 30° C. in the presence of air. By the term "appreciable" is meant that the above testing procedure does not result in sufficient ring-opening of epoxide functionality so as to render the resin uncurable by standard epoxy curing agents, e.g., aliphatic or aromatic amine, anhydride or carboxylic acid curing agents. Preferably less than about 20 percent of the originally available epoxide functionality is degraded according to the above testing procedure. More preferably, less than about 10 percent of the originally available epoxide functionality is degraded. Most preferably, greater than 95 percent of the originally available epoxide functionality remains after exposure for 30 days to air at temperatures of about 30° C.

In the practice of the present invention, the desired reaction product advantageously is recovered from the reaction in commercially suitable form. No purification is required before employing the epoxy phosphate ester resin in a coating formulation or in other suitable applications. The presence of residual water, such as that remaining from the hydrolysis process, in the resulting composition has not been found to be disadvantageous. The presence of water, within the limits described hereinabove, e.g., water of hydrolysis, gives rise to monohydrolyzed oligomers which contribute to the thixotropic and curing properties of the resin. However, too much residual water can result in increased hydrolysis of the epoxide functionality.

The absence of formation of viscous gels or nonsoluble precipitates even upon dilution of solutions with methylene chloride to as much as 2 percent resin content indicates the substantial absence of cross-linked reaction products formed by reaction of phosphoric acid and epoxide functionality. Liquid chromatography, mass spectroscopy, $P^{31}$ nuclear magnetic resonance, and fluorescence spectroscopy indicate that the orthophosphate ester is chemically bonded to the resin backbone containing at least one oxirane functionality.

Curing of resinous epoxy phosphates is readily accomplished by contacting these phosphates with a curing agent, optionally at elevated temperatures. Coatings and molded articles are readily prepared using conventional equipment and techniques. Standard additives including fillers, pigments, dyes, solvents, etc., may be incorporated into the coating or molding composition according to techniques well-known in the art.

When employed as an intumescent coating, e.g., for metal parts employed in construction and other applications, coatings comprising the epoxy phosphate compositions prepared by the present process possess improved adhesion to ferrous metals. Advantageously, mechanical means of increasing adhesion such as attaching reinforcing mesh prior to coating may be eliminated when employing coatings comprising the epoxy phosphate compositions prepared by the present process. Therefore, labor costs associated with the application of the resins of the present invention can be significantly reduced as compared to labor costs for resins which require mechanical adhesion aids.

SPECIFIC EMBODIMENTS

Having described the invention, the following examples are provided as further illustration thereof and are not to be construed as limiting.

EXAMPLE 1

Phosphorus pentoxide in methylene chloride solvent is contacted with butoxyethanol in the ratio of two moles of butoxyethanol for each mole of phosphorus pentoxide. Removal of methylene chloride solvent by evaporation under reduced pressure at a temperature of about 60° C. results in a dark brown oilish liquid identified by $P^{31}$ nuclear magnetic resonance spectroscopy (NMR) as a composition corresponding substantially to the formula:

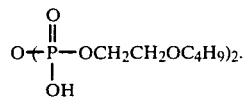

The diester is contacted (neat) with water in the molar ratio of water to diester of 6:1 at a temperature of 25° C. for three hours. The resulting liquid product and excess unreacted water are controllably added with vigorous stirring over a period of about one-half hour to a 12-fold molar excess of a liquid epoxy ether (DER 330, available from The Dow Chemical Company, can be suitably employed) at about 80° C. under nitrogen atmosphere. The reaction is continued for about two hours.

The resulting product is a thick, tan-colored resin having the consistency of taffy at ambient temperatures. Epoxy content (percent epoxide by weight) as determined by standard titration techniques is 14 percent (theoretical maximum percent epoxide is 18.3). After storage for 30 days at 25° C. in contact with air, the percent epoxide is 13.8 percent. Thus, the percent of original epoxide functionality remaining after 30 days is $13.8 \div 14 = 98.6$ percent. Phosphorus content of the resin is approximately 1.3 percent by weight.

EXAMPLES 2-9

The reaction conditions of Example 1 are substantially repeated employing various atmospheres, molar ratios of epoxide:pyrophosphoric acid diester, and water:pyrophosphoric acid diester; these conditions are further identified in Table I. Percent epoxide initially and after exposure for 5 and 30 days to ambient conditions, respectively, are contained in Table I. Table I also indicates the amount of monophosphate ester present in the reaction product as determined by $P^{31}$ nuclear magnetic resonance.

Examples 1-2 demonstrate the preferred technique wherein the organic solvent, methylene chloride, is removed prior to hydrolysis of the diester. Examples 3-9 illustrate the technique wherein the organic solvent is not removed prior to the hydrolysis. The products of Examples 1-2 exhibit superior resistance to degradation over a period of 30 days, i.e., the products of Examples 1-2 are very storage stable.

EXAMPLES 10-15

A sample of resin, which is prepared substantially according to the procedure of Example 1 (1.3 percent phosphorus), is cured using commercially available epoxy resin curing agents, dicyandiamide (DICY), triethylenetetraamine (TETA), and tetrahydrophthalic anhydride (THPA). The gel time of polymer formation is determined by adding 100 percent or 75 percent of a stoichiometric amount of the curing agent along with an accelerator, benzyldimethylamine (BDMA). The curing agent in a solvent solution is added to an acetone solution of the epoxy resin at an elevated temperature. The reaction mixture is stirred until fibers are no longer capable of being drawn from the mixture. The elapsed time to reach this rubbery state is the gel time. Results are contained in Table II.

TABLE II

| Example | Curing Agent | Amount (%) | Temp (°C.) | Gel Time (sec) |
|---|---|---|---|---|
| 10 | DICY/BDMA | 100 | 175 | 509 |
| 11 | DICY/BDMA | 75 | 175 | 611 |
| 12 | TETA | 100 | 120 | 301 |
| 13 | TETA | 75 | 120 | 396 |
| 14 | THPA/BDMA | 100 | 175 | 347 |
| 15 | THPA/BDMA | 75 | 175 | 385 |

EXAMPLES 16-23

Cured and uncured samples of epoxy resin are tested for residual char formation by heating in a DuPont 1090 Thermal Analyzer at 600° C. in an air atmosphere to determine residual char. Accordingly, a weighed amount of the cured resin prepared substantially according to the provisions of Examples 1 or 11 and standard epoxy resins with or without phosphorus additives (to give 1.3 percent phosphorus content) are tested. Residual char formation is expressed as percent by weight of original resin. Results are contained in Table III.

TABLE III

| Example | Epoxy Resin | Additive (1.3% P) | % Char |
|---|---|---|---|
| 16 | Ex. 1 (uncured) | — | 23.7 |
| 17 | Ex. 11 (cured) | — | 22.4 |
| 18 | DER-330 (uncured)[1] | — | 4.6 |
| 19 | DER-330 (cured)[2] | — | 9.5 |
| 20 | DER-661 (uncured) | — | 2.1 |
| 21 | DER-661 (cured)[1] | — | 9.0 |
| 22 | DER-661 (uncured) | $Ph_3P=O$ | 14.3 |
| 23 | DER-330 (cured) | $Ph_3P=O$ | 16.5 |

[1] An epoxy resin of approximately 360 mole weight available from The Dow Chemical Company.
[2] Cured with DICY, 100 percent of theoretical.

TABLE I

| Example | Molar Ratios epoxide/diester | Molar Ratios H₂O/di-ester | ATM | % Epoxide Theory | % Epoxide Initial | % Epoxide 5-day | % Epoxide 30-day | Stability* | Area % monophosphate ester |
|---|---|---|---|---|---|---|---|---|---|
| 1 | 12.0 | 6.0 | N₂ | 18.3 | 14.0 | — | 13.8 | 98.6 | 96.2 |
| 2 | 12.0 | 10.0 | N₂ | 18.3 | 12.3 | — | 12.0 | 97.6 | 95.5 |
| 3 | 8.0 | 3.5 | N₂ | 16.0 | 16.7 | 14.7 | 10.2 | 61.1 | 95.0 |
| 4 | 12.0 | 4.0 | N₂ | 18.3 | 16.7 | 12.4 | 12.8 | 76.6 | 95.5 |
| 5 | 16.0 | 4.0 | N₂ | 19.6 | 17.3 | 14.8 | 14.3 | 82.7 | 95.5 |
| 6 | 17.4 | 1.3 | N₂ | 20.1 | 18.1 | 16.4 | 16.2 | 89.5 | 62.0 |
| 7 | 17.4 | 2.5 | N₂ | 20.1 | 16.6 | 14.6 | 14.6 | 88.0 | 80.0 |
| 8 | 17.4 | 3.6 | Air | 20.1 | 16.3 | 14.5 | 14.0 | 85.9 | 91.1 |
| 9 | 17.4 | 5.0 | N₂ | 20.0 | 16.6 | 13.8 | 13.8 | 83.1 | 98.0 |

*Percentage of original epoxide remaining after 30 days.

It is seen that epoxy resins according to the present invention have significantly improved residual char compared to conventional epoxy resins and, compared to conventional resins, contain equivalent amounts of phosphorus-containing additive.

What is claimed is:

1. A process for preparing a phosphate ester which contains at least one terminal epoxide moiety, the process comprising contacting under reaction conditions, optionally in the presence of water, at least one phosphoric acid ester with an amount of an epoxide having an epoxy equivalent greater than one, said amount being sufficient to substantially neutralize the phosphoric acid functionality of the phosphoric acid ester, the contacting being such that there is formed a composition comprising a phosphate ester containing terminal epoxide functionality and corresponding to the formula:

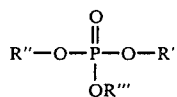

wherein R' is a glycidyl ether of the general formula:

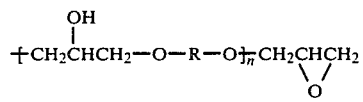

wherein

R is a difunctional remnant of a dihydroxy compound formed by removal of the hydroxyl groups thereof;
R'' is a group as defined by R''' or R';
R''' is an organic group of up to about 20 carbons; and
n is a positive number less than about 20 and is equal to the number of repeating units in the compound.

2. A process for preparing a phosphate ester which contains at least one terminal epoxide moiety, the process comprising:

(1) forming an organic-soluble pyrophosphate diester corresponding to the formula:

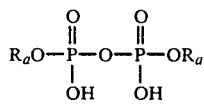

wherein $R_a$ is an organic group of up to about carbon atoms, in an organic solvent;

(2) contacting the organic-soluble pyrophosphate diester with from about 1 to about 16 moles of water per mole of pyrophosphate diester to form the corresponding phosphoric acid monoesters; and (3) contacting at least one phosphoric acid ester of step (2) with an amount of an epoxy having an epoxy equivalent greater than one, said amount being sufficient to substantially neutralize the phosphoric acid functionality.

3. A process according to claim 2 for preparing a composition comprising a phosphate ester containing terminal epoxide functionality corresponding to the formula:

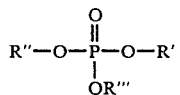

wherein R' is a glycidyl ether of the general formula

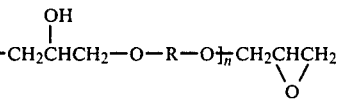

wherein

R is a difunctional remnant of a dihydroxy compound formed by removal of the hydroxyl groups thereof;
R'' is a group as defined by R''' or R';
R''' is an organic group of up to about 20 carbons; and
n is a positive number less than about 20 and is equal to the number of repeating units in the compound.

4. A process according to claim 3 wherein R''' is alkyl or alkoxyalkyl.

5. A process according to claim 3 wherein R''' is 2-n-butoxy ethyl.

6. A process according to claim 2 wherein in step (2) the molar ratio of diester:water is from about 1:2 to about 1:12.

7. A process according to claim 6 wherein in step (2) the molar ratio of diester:water is from about 1:4 to about 1:10.

8. A process according to claim 2 wherein in step (3) the equivalent ratio of epoxy equivalent to acid equivalent is from about 4:1 to about 20:1.

9. A process according to claim 8 wherein in step (3) the equivalent ratio of epoxy equivalent to acid equivalent is from about 6:1 to about 12:1.

10. A process according to claim 2 wherein in step (3) the reaction is conducted at an elevated temperature.

11. A process according to claim 10 wherein in step (3) the reaction is conducted at an elevated temperature of up to about 80° C.

12. A process according to claim 2 wherein in step (2) the addition temperature is about ambient temperature or lower.

13. A composition prepared according to the process of claim 2.

14. A composition of matter comprising a phosphate ester containing terminal epoxide functionality corresponding to the formula:

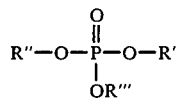

wherein R' is a glycidyl ether of the general formula

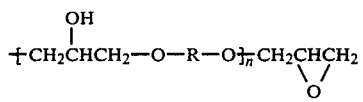

wherein

R is a difunctional remnant of a dihydroxy compound formed by removal of the hydroxyl groups thereof;
R'' is a group as defined by R''' or R';
R''' is an organic group of up to about 20 carbons; and
n is a positive number less than about 20 and is equal to the number of repeating units in the compound.

15. A composition according to claim 14 further characterized as comprising from about 0.5 percent to about 2.6 percent phosphorus by weight.

16. A composition according to claim 15 wherein the phosphorus content is from 0.75 percent to about 1.5 percent phosphorus by weight.

17. A composition according to claim 14 further characterized by possessing an epoxide content from about 5 percent to about 20 percent by weight.

18. A composition according to claim 17 characterized in that the epoxide content after storage at 30° C. for 30 days in the presence of air is from about 4.5 percent to about 18 percent by weight.

19. A composition according to claim 14 wherein R''' is alkyl or alkoxyalkyl.

20. A composition according to claim 14 wherein R''' is 2-n-butoxyethyl.

21. A coating composition having intumescent properties prepared using a composition of matter according to claim 14.

* * * * *

UNITED STATES PATENT AND TRADEMARK OFFICE
CERTIFICATE OF CORRECTION

PATENT NO. : 4,613,661

DATED : September 23, 1986

INVENTOR(S) : Horst G. Langer et al.

It is certified that error appears in the above-identified patent and that said Letters Patent is hereby corrected as shown below:

On the Title Page:

Under the heading entitled "References Cited", please insert --2,013,643 Demarthe et al.--.

Signed and Sealed this

Twenty-second Day of September, 1987

Attest:

DONALD J. QUIGG

Attesting Officer     Commissioner of Patents and Trademarks